(12) United States Patent
Shannon et al.

(10) Patent No.: US 9,616,145 B2
(45) Date of Patent: Apr. 11, 2017

(54) HEALTHCARE FACILITY DISINFECTING SYSTEM

(71) Applicant: Medizone International, Inc., Sausalito, CA (US)

(72) Inventors: Michael Edward Shannon, Picton (CA); Dick Eric Zoutman, Kingston (CA)

(*) Notice: Subject to any disclaimer, the term of this patent is extended or adjusted under 35 U.S.C. 154(b) by 324 days.

(21) Appl. No.: 14/046,535

(22) Filed: Oct. 4, 2013

(65) Prior Publication Data

US 2014/0037499 A1    Feb. 6, 2014

Related U.S. Application Data

(63) Continuation-in-part of application No. 13/343,403, filed on Jan. 4, 2012, now Pat. No. 8,551,399, which is a continuation of application No. PCT/CA2010/000998, filed on Jul. 5, 2010.

(60) Provisional application No. 61/223,219, filed on Jul. 6, 2009, provisional application No. 61/295,851, filed on Jan. 18, 2010.

(51) Int. Cl.
*A61L 2/20* (2006.01)

(52) U.S. Cl.
CPC .............. *A61L 2/202* (2013.01); *A61L 2/208* (2013.01); *A61L 2202/11* (2013.01); *A61L 2202/13* (2013.01); *A61L 2202/14* (2013.01); *A61L 2202/25* (2013.01)

(58) Field of Classification Search
CPC .................................. A61L 2/202; A61L 2/208
See application file for complete search history.

(56) References Cited

U.S. PATENT DOCUMENTS

| | | | |
|---|---|---|---|
| 5,316,741 | A | 5/1994 | Sewell et al. |
| 5,666,640 | A | 9/1997 | Daniylchev |
| 6,045,846 | A | 4/2000 | Bautista et al. |

(Continued)

FOREIGN PATENT DOCUMENTS

| | | |
|---|---|---|
| CA | 2473540 | 7/2003 |
| CA | 2486831 A1 | 2/2004 |

(Continued)

OTHER PUBLICATIONS

"Ozone effects on bacteria, molds and viruses—ozone and bacteria destruction", published Dec. 24, 2007, http://web.archive.org/web/20071224191320/http://www.ozoneapplications.com/info/ozone_bacteria_mold_viruses.htm.

(Continued)

*Primary Examiner* — Sean E Conley
*Assistant Examiner* — Donald Spamer
(74) *Attorney, Agent, or Firm* — Durham Jones & Pinegar, P.C. Intellectual Property Law Group

(57) ABSTRACT

A system and process for disinfecting rooms such as health care facility rooms with an oxygen/ozone mixture is described, which is effective to combat "superbugs" such as *Clostridium difficile* (*C. difficile*); *E. coli*; *Pseudomonas aeruginosa*; methicillin-resistant *Staphylococcus aureus* (MRSA); and vancomycin-resistant *Enterococcus* (VRE). In preferred embodiments, hydrogen peroxide is additionally used. The system and process is effective to destroy bacteria deposited on surfaces as biofilm, and, accompanied by physical agitation such as jet nozzle outlets, is effective to disinfect carpet, drapery and similar absorbent and porous surfaces.

16 Claims, 5 Drawing Sheets

(56) References Cited

U.S. PATENT DOCUMENTS

| | | | |
|---|---|---|---|
| 7,217,685 | B2 | 5/2007 | McDonnell et al. |
| 7,393,818 | B2 | 7/2008 | McDonnell et al. |
| 7,407,624 | B2 | 8/2008 | Cumberland et al. |
| 8,551,399 | B2 | 10/2013 | Shannon et al. |
| 8,636,951 | B2 | 1/2014 | Shannon et al. |
| 2003/0039729 | A1 | 2/2003 | Murphy et al. |
| 2003/0132279 | A1 | 7/2003 | Stemmle |
| 2004/0003511 | A1* | 1/2004 | Silver .............................. 34/201 |
| 2005/0129571 | A1 | 6/2005 | Centanni |
| 2005/0226764 | A1 | 10/2005 | Moirandat et al. |
| 2006/0104858 | A1 | 5/2006 | Potember et al. |
| 2007/0079455 | A1 | 4/2007 | Brewer et al. |
| 2007/0086914 | A1 | 4/2007 | Antinozzi |
| 2008/0031770 | A1 | 2/2008 | Heselton et al. |
| 2009/0047174 | A1* | 2/2009 | Hill .................................. 422/28 |
| 2009/0263499 | A1 | 10/2009 | Platt, Jr. et al. |
| 2012/0020832 | A1* | 1/2012 | St. Onge ................. A61L 9/015 422/4 |

FOREIGN PATENT DOCUMENTS

| | | |
|---|---|---|
| CA | 2491781 | 7/2005 |
| CA | 2547589 | 7/2005 |
| CA | 2526367 | 4/2007 |
| WO | 2004011041 A2 | 2/2004 |
| WO | 2005060385 A2 | 7/2005 |
| WO | 2009046562 | 4/2009 |
| WO | 2011003179 A1 | 1/2011 |

OTHER PUBLICATIONS

"Prospects for Managed Underground Storage of Recoverable Water", National Research Council, 2008, p. 243.
Wenzel et al., "The Impact of Hospital-Acquired Blood-stream Infections", Emerging Infectious Diseases, vol. 7, No. 2, Mar.-Apr. 2001, pp. 174-177.
Matz et al., "Biofilm Bacteria Protect Themselves With Chemical Weapons", Helmholtz Centre for Infection Research, Bauschweig, reported on Inforniac.com, Jul. 23, 2008.
PCT Written Opinion of the International Searching Authority for PCT Application No. PCT/CA2010/000998, Oct. 7, 2010, 11 pages.
PCT International Preliminary Report on Patentability for PCT Application No. PCT/CA2010/000998, Jul. 27, 2011, 17 pages.
PCT Notification of the Recording of a Change for PCT Application No. PCT/CA2010/000998 (adding Dick Eric Zoutman as an inventor), Mar. 17, 2011, 1 page.
Amendment Under Article 34 to PCT Application No. PCT/CA2010/000998, Mar. 1, 2011, 7 pages.
Amendment Pursuant to Article 19 of the Patent Cooperation Treaty for PCT Application No. PCT/CA2010/000998, Dec. 2, 2010, 14 pages.
United States Patent and Trademark Office, "Comments on Statement of Reasons for Allowance," filed Sep. 6, 2013 in U.S. Appl. No. 13/343,403 in response to Notice of Allowability dated Aug. 2, 2013.
Canadian Intellectual Property Office, "International Search Report and Written Opinion" issued in International Patent Application No. PCT/CA2011/050542 dated Dec. 9, 2011.
Canadian Intellectual Property Office, "International Search Report and Written Opinion" issued in International Patent Application No. PCT/CA2011/050543 dated Dec. 19, 2011.
Canadian Intellectual Property Office, "International Search Report and Written Opinion" issued in International Patent Application No. PCT/CA2011/050544 dated Dec. 28, 2011.
United States Patent and Trademark Office, "Notice of Allowability" issued in U.S. Appl. No. 13/343,403 dated Aug. 2, 2013.
Canadian Intellectual Property Office, "International Search Report and Written Opinion," issued in International Patent Application No. PCT/CA2010/001364, dated Dec. 3, 2010.
Rogers et al., "Bacillus anthracis Spore Inactivation by Fumigant Decontamination", Applied Biosafety, 2008, vol. 13, No. 2, pp. 89-98, available at http://www.absa.org/abj/abj/081302Rogers.pdf.
United States Environmental Protection Agency, "US Environmental Protection Agency Office of Pesticide Programs List H: EPA's Registered Products Effective Against MRSA and VRE," Jan. 9, 2009.
Whitney et al., "Inactivation of Bacillus anthracis Spores", Emerging Infectious Diseases, Jun. 2003, vol. 9, No. 6, pp. 623-627, available at http://wwwnc.cdc.gov/eid/article/9/6/pdfs/02-0377.pdf.

* cited by examiner

HEALTHCARE FACILITY DISINFECTING SYSTEM

CROSS-REFERENCE TO RELATED APPLICATIONS

This application is a continuation-in-part application of allowed U.S. patent application Ser. No. 13/343,403, filed on Jan. 4, 2012 and titled HEALTHCARE FACILITY DISINFECTING SYSTEM, now U.S. Pat. No. 8,551,399, which application is a continuation of, and claims priority to and the benefit of, PCT International Application No. PCT/CA2010/000998 filed Jul. 5, 2010, designating the United States and published Jan. 13, 2011 as International Publication No. WO/2011/003179, which application claims priority to and the benefit of U.S. Provisional Patent Application No. 61/223,219 filed on Jul. 6, 2009, and U.S. Provisional Patent Application No. 61/295,851 filed on Jan. 18, 2010. This application is also related to Canadian Patent No. 2,735,739 issued on Nov. 22, 2011, which Canadian patent also claims priority to and the benefit of PCT International Application No. PCT/CA2010/000998. The disclosures of the above-identified patents and applications are expressly incorporated herein by this reference in their entireties.

FIELD OF THE INVENTION

This invention relates to disinfecting systems for use in healthcare facilities, public health facilities and the like, to eliminate or at least to reduce to acceptable levels, microbial residues which are resistant to conventional disinfectant and sterilization systems.

BACKGROUND OF THE INVENTION

Despite intensive preventive efforts over the past several years in hospital and other healthcare facilities, the incidence of life threatening infections caused by a growing array of antibiotic resistant bacteria (sometimes referred to as "superbugs") has grown significantly and is now posing a serious problem for medical staff worldwide. According to an editorial in the journal "Science" (July 2008), the number of deaths in 2006 attributable to bacterial infections in healthcare facilities in the United States exceeded the U.S. death toll attributed to HIV/AIDS in the same year, and probably result in as many as 70,000 deaths per year in the United States. This is despite the best efforts of healthcare personnel properly to clean their facilities and the equipment contained therein.

The major causative agents (bacteria) for hospital-based infections (nosocomial infections) are *Clostridium difficile* (*C. difficile*); *E. coli; Pseudomonas aeruginosa*; methicillin-resistant *Staphylococcus aureus* (MRSA); and vancomycin-resistant *Enterococcus* (VRE).

Approximately 5% of all acute care hospitalizations in the U.S. develop a nosocomial infection with an incidence rate of five infections per thousand patient days, and early estimates of the added expenditure are in excess of $4.5 billion (Wentzel R, Edmond M D, "The Impact of Hospital Acquired Blood Stream Infections," *Emerg. Inf. Dis.*, March-April 2001:7(174)). A more recent estimate of the aggregate direct hospital cost for nosocomial infections in 2007 (R D Scott, CDC, March 2009) was between $35.7 and $45.0 billion. When this rate is applied to the 35 million patients admitted to 7,000 acute-care institutions in the U.S., it is estimated that there are more than 2 million cases per year. Nosocomial infections are estimated to double, at least, the mortality and morbidity risks of any admitted patient.

The significant, and growing, incidence of antibiotic resistant bacteria in healthcare facilities has been termed by some as a "Silent Epidemic". On the international scene, a World Health Organization survey of 55 hospitals in 14 countries representing four WHO regions (Europe, Eastern Mediterranean, South-East Asia and Western Pacific) reported that an average of 8.7% of hospital patients had nosocomial infections. The WHO estimates that, at any time, over 1.4 million people worldwide suffer from infection acquired in a hospital.

Of particular concern in this context are the bacteria *C. difficile* and MRSA. Until recently, *C. difficile* was relatively uncommon, but has now become epidemic in many regions of the world. Indeed, it is now recognized by a growing number of public health officials as a worldwide epidemic (pandemic) with incalculable financial and health implications. MRSA has been identified by the American Academy of Orthopaedic Surgeons as the single biggest concern for surgical procedures, and concurs with recent journal articles that it constitutes a "silent epidemic." Under current healthcare facility cleaning and sterilizing procedures, both *C. difficile* and MRSA, as well as the aforementioned *E. coli; Pseudomonas aeruginosa*; and vancomycin-resistant *Enterococcus* (VRE), are ineffectively treated and subsequently removed, so that colonies of these pathogens accumulate in healthcare facilities, especially on porous surfaces such as carpets and drapes.

Attempts to combat and kill nosocomial infections caused by bacteria such as *Pseudomonas aeruginosa* and *Staphylococcus aureus* are hampered by the fact that the bacteria grow within biofilms that protect them from adverse environmental factors. A biofilm is an aggregate of microorganisms in which cells adhere to each other and/or to a surface. They are frequently embedded in a self produced matrix of extracellular polymeric substance (EPS), a polymeric conglomeration generally composed of extracellular DNA, proteins and polysaccharides. Biofilms form on surfaces, e.g. in hospital settings, in the presence of water vapor.

Free floating microorganisms in planktonic (single cell) mode attach to a surface, and if not immediately removed, will anchor themselves more permanently to the surface. These first colonists provide more diverse adhesion sites for the arrival of other cells, thus beginning to build a matrix that holds the biofilm together and provides additional anchoring sites for arriving cells. The biofilm grows through a combination of cell division and recruitment. When the biofilm is established, the aggregate cell colonies are apparently increasingly antibiotic resistant. It has also been reported that biofilm bacteria apply chemical weapons to defend themselves against disinfectants and antibiotics (see "Biofilm Bacteria Protect Themselves With Chemical Weapons", Dr. Carsten Matz et. al., Helmholtz Centre for Infection Research, Brauschweig, reported on Informiac.com, Jul. 23, 2008).

Bacteria living in a biofilm have significantly different properties from the planktonic form of the same species, as the dense and protected environment of the film allows them to co-operate and interact in various ways. Traditional hospital cleaning procedures and solutions are usually not sufficient to eradicate long term contaminations, and one major reason for their persistence seems to be the capability of the bacteria to grow within biofilms that protect them from adverse environmental factors.

Also of growing concern are threatened bioterrorist and warfare attacks using potentially lethal bacteria. Some of the deadliest bacteria, for example anthrax, are highly resistant to conventional sterilization agents and treatments. Contamination of public facilities with such bacteria constitutes a significant threat to human life with residual amounts of such bacteria being almost impossible to remove using current methods.

BRIEF REFERENCE TO THE PRIOR ART

Current procedures for the sanitization of hospitals and other healthcare facilities have become increasingly ineffective, resulting in the accumulation of deadly bacteria throughout the facilities. Rising costs of the provision of healthcare in most if not all countries militate against spending more than the minimum time and effort on cleaning and sterilizing procedures.

Chlorinated solutions with and without ammonia are commonly used, but have shown only limited success. To add to this challenge, such solutions cannot be used on electronic devices commonly installed in wards, recovery rooms, operating theaters, etc.

Vaporized hydrogen peroxide (VHP) is highly effective when applied to smooth surfaces, but has little or no efficacy on porous materials and fabrics. Moreover, VHP is very damaging to electronic devices.

Once a non-medical surface such as carpet, drapery, bedding, porous material in ceilings and the like becomes impregnated with highly resistant pathogens, especially spore formers such as *C. difficile*, it cannot be effectively disinfected using currently available agents and processes.

Ozone is known to be a powerful anti-bacterial, anti-fungal and anti-viral agent. For over 100 years, it has been used for water purification. It is known to be effective against *Legionella* Bacteria, *E. coli* and *pseudomonas* populations in such plants.

Ozone use in healthcare facilities is, however, problematic. Solutions containing high concentration of ozone are explosive on warming. Ozone is medically harmful to those exposed to it, causing irritation of eyes and mucous membranes, pulmonary edema, and chronic respiratory disease if low, safe levels of exposure are exceeded. Moreover, it is widely recognized to be an environmental hazard.

Canadian Patent 2,486,831 (Arts et al.), issued Jul. 12, 2011, discloses the use of a combination of ozone and UV radiation for decontamination of air in a room such as a mobile isolation unit, a hospital room and the like. The air is caused to flow through a portable unit containing a filter exposed to ozone.

U.S. Pat. No. 7,407,624 (Cumberland et al.), issued Aug. 5, 2008, describes methods for abating allergens, pathogens, odors and volatile organic compounds in air, using an atmosphere having specific combinations of ozone concentration, hydrogen peroxide concentrations, temperature and humidity delivered over a specified period of time. The patent contains only one experimental account, namely, of treating rooms of a residence (a house) for *cladosporium* mold spores and *penicillium/aspergillus* molds in the room air. No details of the precise conditions used are given. There is no demonstration or disclosure of treatment of contaminated surfaces in a room. The general disclosure of the patent states that selected conditions of ozone concentration, hydrogen peroxide, humidity and temperature are highly effective in killing airborne molds and fungi at ozone concentrations below 6-9 ppm, but the precise conditions used are not disclosed. There is no teaching of any range of ozone and hydrogen peroxide concentrations in combination, or of other conditions of their use, which would be effective against, for example, MRSA or *C. Difficile*.

There is thus a need for a safe, effective but inexpensive system for disinfecting rooms of healthcare facilities, including all the contents therein. Such a system should drastically reduce (99.999% or greater) the amounts of at least the five aforementioned bacteria in all contaminated spaces to be of clinical and public health value. Furthermore, this level of microbial decontamination must be achieved such that the space is only removed from healthcare use for a minimum period of time, while remaining safe and harmless with respect to electronic and other equipment in the room. Accordingly, the decontamination process should not require that the space in question be emptied of its contents while the system is operated.

SUMMARY OF THE INVENTION

The present invention provides, from one aspect, an ozone and hydrogen peroxide-based disinfection system for rooms and their contents within all healthcare facilities, mobile or stationary, and other critical infrastructure such as schools and government buildings. Using such a system, a gaseous disinfecting atmosphere comprising ozone and hydrogen peroxide is delivered into and applied to the surfaces and equipment and objects contained within the room. The application can be through simple contact of the gaseous atmosphere with the surfaces, or, in the case of difficult-to-clean surfaces such as drapes, carpets and other fibrous surfaces, it can be by means of a dislodgement system effecting physical agitation of the surface (scrubbing brushes, high pressure jets or the like, sometimes referred to herein as "scrubbing"). The gaseous disinfecting atmosphere is applied at controlled concentrations and, in some cases, elevated pressures which have been found to be effective in destroying critical viral, bacterial and fungal pathogens found in environments, including but not limited to the five especially troublesome bacteria *Clostridium difficile* (*C. difficile*); *E. coli*; *Pseudomonas aeruginosa*; methicillin-resistant *Staphylococcus aureus* (MRSA); and vancomycin-resistant *Enterococcus* (VRE). It has also been found that using such controlled concentrations at atmospheric pressure can be effective against such bacteria in conditions which improve exposure of the bacteria to the disinfecting atmosphere, preferably for example conditions wherein movement of the disinfecting atmosphere over the bacteria is minimized. Operating at atmospheric pressure is typically an administrative requirement for using the present invention in hospitals in order to reduce the risk of leakage of ozone and hydrogen peroxide out of a room under treatment if operated at elevated pressure. However, the effectiveness of the ozone and hydrogen peroxide protocols of the present invention would be reduced to unsatisfactory levels absent use of further steps to compensate for operating at atmospheric pressure. Such further conditions preferably include minimizing movement of the disinfecting atmosphere over the bacteria located on surfaces in the room during treatment of the room. This may be achieved, preferably, by suspending application of force(s) promoting movement of the disinfecting atmosphere in the room under treatment for a sufficient time to permit those parts of the disinfecting atmosphere in contact with the bacteria to have an extended time of contact with the bacteria and thereby extend the period of time of action of such parts of the disinfecting atmosphere on the bacteria. Suspension of the application of force(s) promoting movement of the disinfecting atmosphere may be performed one or more times during the treatment of the room, preferably in two or more intervals. Further preferably the total time of suspension of the application of force(s) promoting movement of the disinfecting atmosphere during the treatment of the room is up to about 60% of the total treatment time, more preferably about 50% of the total treatment time and most preferably about from 20% to about 40% of the total treatment time.

In addition to effectively eliminating aerosolized pathogens within a given space, the system of the invention also allows an operator to apply the ozone and hydrogen peroxide-containing gases at respectively predetermined concentrations of ozone and hydrogen peroxide directly to problem surfaces, such as textiles, in the room, with a localized physical agitation action and under localized pressure where appropriate. The system may operate in the room at a pressure above atmospheric with or without such physical agitation and localized pressure, or at atmospheric pressure with such physical agitation and localized pressure and/or with minimization of movement of the disinfecting atmosphere as discussed above. The system also preferably includes an ozone-destruct unit for removing residual ozone from the room atmosphere and a hydrogen peroxide removal/destruct unit. The whole system is portable, so that it can be moved from room to room as required, and is harmless to equipment contained in the room. Once the sterilization process is completed, the room can be back in medical use within as little as 20 minutes depending on the amounts of ozone and hydrogen peroxide used, with its residual atmospheric ozone level at an acceptable 0.04 ppm or less and hydrogen peroxide below 1.00 ppm, preferably at or below 0.75 ppm.

BRIEF REFERENCE TO THE DRAWINGS

FIG. 1 of the accompanying drawings is a diagrammatic illustration of an apparatus in accordance with an embodiment of the invention, disposed within a room to be disinfected;

DETAILED DESCRIPTION

Figure 1:
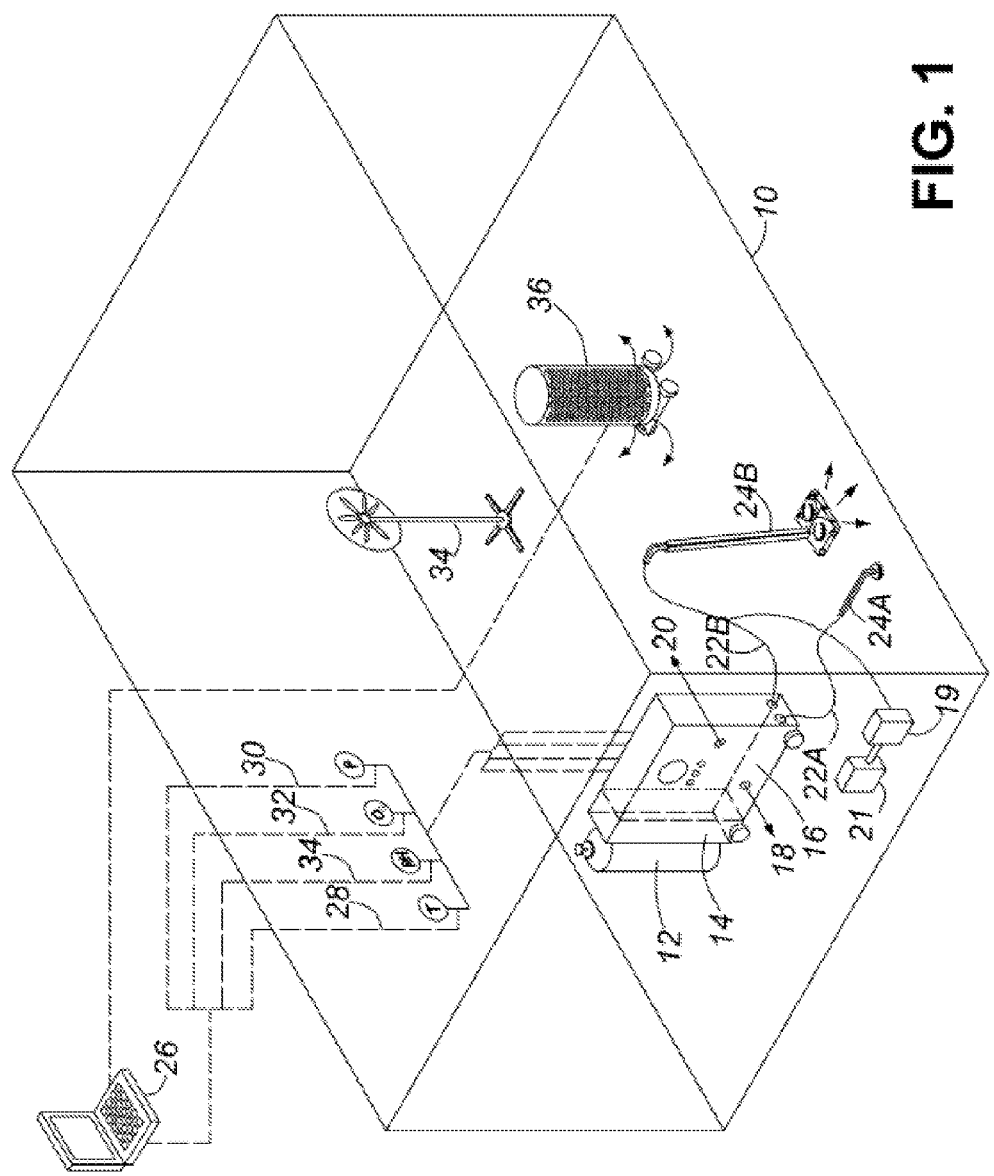

One significant feature of the system according to certain embodiments of the invention is the ability to adjust the pressure of the ozone/hydrogen peroxide/oxygen gas mixture being used for disinfection purposes. It has been found that, in many cases in appropriate settings, effective disinfection of a room and its contents from bacterial contamination can best be achieved by pressurizing the atmosphere in the room with an ozone/hydrogen peroxide/oxygen mixture achieving a pressure higher than normal atmospheric pressure, e.g. from about 14.7 psi to about 100 psi. Alternatively, a localized, directed stream of such mixture, i.e. as a pressurized air jet can also be used, which would be one way to obviate the need to raise the overall pressure in the room. Raising the room pressure may require initial sealing of the room prior to the decontamination process. With many rooms where medical procedures are conducted, such as operating theatres, this is a simple process, since such rooms are designed to be substantially sealed when in use for medical procedures. With other rooms, this may require some significant initial preparation. Preferably, however, due partly to hospital administration concerns for safety, the system of the invention is operated without elevating atmospheric pressure in the treatment room as this greatly reduces the risk of leakage of the treatment gas mixture out of the room where it may affect unprotected people, equipment, furnishings, décor, etc. This is achieved by having all ozone generation and removal occur within the room being treated, as opposed to having external generation and gas administration through a delivery port. The latter would create unacceptable, largely continuous, air/gas currents and higher than atmospheric pressure in the room under treatment.

The invention utilizes hydrogen peroxide, as well as ozone, in the disinfecting gaseous atmosphere. When using ozone and hydrogen peroxide, increasing the pressure within the room may not be necessary. The particularly troublesome bacteria which are likely to cause nosocomial infections in a hospital environment, namely *Clostridium difficile* (*C. difficile*); *E. coli*; *Pseudomonas aeruginosa*; methicillin-resistant *Staphylococcus aureus* (MRSA); vancomycin-resistant *Enterococcus* (VRE), deposit on surfaces in a hospital environment such as stainless steel surfaces, ceramic surfaces and marble surfaces and quickly form or are captured by a biofilm in which the microorganisms thrive. Treatment with the combination of hydrogen peroxide and ozone, at appropriate humidity, according to this preferred aspect of invention, destroys the bacteria in the biofilm, either by chemically attacking the biofilm to expose the microorganisms to the biocidal action of the ozone and hydrogen peroxide, or by interference of the bacterial cells' activity in the biofilm by the ozone/hydrogen peroxide combination employed, or by a combination of these, possibly with other, mechanisms.

Thus according to this preferred embodiment of the present invention, from one aspect, there is provided a process of combating bacteria in an enclosed space within a room and contained in biofilm on surfaces within the room, which comprises:

creating in the room a disinfecting atmosphere which includes ozone at a concentration of 2-350 ppm by weight and hydrogen peroxide at an amount of 0.2-10 wt. %, preferably 1.0-10 wt. %, at a relative humidity of at least 60%, wherein the amount of hydrogen peroxide is derived from a supply solution of 0.2-10% hydrogen peroxide;

subjecting the biofilm, including at least biofilm carrying surfaces having live bacteria therein, to the disinfecting atmosphere for a period of time effective to cause substantial kill, by at least a 6 log reduction, of the bacteria in the biofilm, the period of time being at least 20 minutes, preferably at least 30 minutes; and subsequently removing ozone from the atmosphere, down to 0.04 ppm or less, and removing peroxide from the atmosphere, down to 0.75 ppm or less.

Preferably the disinfecting atmosphere has a relative humidity of at least 65%.

When use of elevated pressure in the treatment room is contraindicated, the process also comprises maintaining atmospheric pressure in the room during the treatment. However, in order still to achieve effective kill of the bacteria in the biofilm at atmospheric pressure, the step of exposing the biofilm surfaces to the disinfecting atmosphere for at least 30 minutes further preferably includes suspending, for up to 60% of the exposure time, application of force(s) causing movement of the disinfecting atmosphere. Such suspension need only be long enough to allow for those parts of the disinfecting atmosphere in contact with the bacteria to have a sufficiently extended time of contact with the bacteria to permit effective kill of the bacteria. More preferably such time is up to 50% of the exposure time (i.e. 50% of the total time of treatment of the room). Further preferably this is from 20% to 40% of the exposure time. Suspension of the application of force(s) promoting movement of the disinfecting atmosphere may be performed one or more times during the treatment of the room, preferably in two or more intervals. In a particularly preferred embodiment in which the ozone/hydrogen peroxide gas is with force introduced to the room up to desired concentrations and then maintained at approximately those concentrations throughout the treatment time by further introductions of such gas with force at intervals, as necessary, wherein the force is preferably applied using a fan, the times between the further introductions of such gas are collectively calculated to provide the aforementioned preferred times of suspension of the application of force(s).

Another preferred embodiment provides a process for disinfecting a room and surfaces therein to combat at least one of the microorganisms bacteria *Clostridium difficile* (*C. difficile*); *E. coli; Pseudomonas aeruginosa*; methicillin-resistant *Staphylococcus aureus* (MRSA); vancomycin-resistant *Enterococcus* (VRE); *Bacillus subtilis*, and/or anthrax, which comprises exposing the room and surfaces therein to a gaseous atmosphere which includes an effective amount of ozone and an effective amount of hydrogen peroxide, for a period of time which substantially reduces levels of bacteria on the surfaces, and subsequently removing the residual ozone in the room's atmosphere, down to a safe low level.

The process is particularly effective with or without physical agitation, in disinfection of stainless steel surfaces which abound in medical treatment facilities, and on which bacteria are tenacious and difficult to destroy, due at least in part to their generation of a biofilm on such surfaces. The process is also effective in destroying and deactivating anthrax bacteria, as evidenced by its effectiveness against the well-established anthrax surrogate *Bacillus subtilis.*

According to another aspect of this embodiment, there is also provided a portable system for rapidly disinfecting rooms, surfaces and equipment therein, comprising:

- an ozone generator for discharging into the room a gaseous mixture including ozone;
- an ozone controller adapted to control the amount of discharged ozone;
- a source of hydrogen peroxide for discharging controlled amounts of hydrogen peroxide into the room;
- means for discharging the hydrogen peroxide and ozone into the room;
- humidity adjusting means adapted to increase or decrease the relative humidity of the room during treatment; and
- an ozone remover adapted to destroy ozone, down to a safe level in the room atmosphere for subsequent human utilization.

It is sometimes beneficial, in appropriate applications, to increase the effectiveness and shorten the duration of the process, to operate at elevated pressure when using ozone and hydrogen peroxide in the disinfecting gas. Thus, according to another aspect of the present invention, there is provided a process for disinfecting a room of a healthcare facility, which comprises:

- introducing into the room a gas mixture which includes ozone and hydrogen peroxide in effective amounts;
- raising the pressure within the room above atmospheric pressure, or introducing a pressurized gas stream;
- physically agitating fibrous and porous surfaces within the room while the surfaces are exposed to the pressurized gas stream of hydrogen peroxide and ozone containing atmosphere of relative humidity at least 60%;
- returning the room to atmospheric pressure; and
- removing the residual ozone from the room's atmosphere, down to a safe level.

Preferred ozone amounts are from about 20-350 parts per million in the treatment gas atmosphere, more preferably 20-200 parts per million, even more preferably 20-90 parts per million, and most preferably 35-80 ppm ozone. Preferred amounts of hydrogen peroxide are the amounts supplied to the room treatment atmosphere using an aqueous solution containing 0.2-10%, more preferably 0.5-10% or 1.0 to 10%, further preferably 0.5-5%, and most preferably 1-5%, hydrogen peroxide. In the description below, the peroxide percentages used are sometimes expressed in terms of these solution percentages. The amounts are chosen so that no serious deleterious effects are suffered by other equipment in the treatment room. The amount of hydrogen peroxide in the disinfecting atmosphere can be calculated from the volume of aqueous hydrogen peroxide evaporated into the disinfecting atmosphere, the volume of the room being disinfected and the concentration of hydrogen peroxide in the starting solution. Times of exposure of the room and its surface to the ozone-containing atmosphere are suitably from 30 minutes to about 120 minutes, preferably from about 60 to about 105 minutes, and most preferably about 90 minutes. These times are constrained to some extent by the need to clear the room of ozone (down to a maximum of 0.04 ppm) following the disinfection phase, and return the room to medical use within a reasonable period of time, with the entire start-to-finish time not exceeding 150 minutes. The ozone removal is an extremely rapid and fully effective process. Both the hydrogen peroxide and the ozone (and any products of interaction between them) should be removed before the room is put back into normal use.

Another significant feature of preferred embodiments of the present invention is the provision of a dislodgement system at the outlet end of the discharge. The dislodgement system allows penetration of carpet, drape and similar surfaces in the room, to gain access to concealed/sequestered spores and/or colonies of bacteria. The dislodgement system can be manually operated, with operators protected by a hazard suit and mask, or remotely operated or totally automated. It may take the form of one or more outlet jets, with associated manually operable jet pressure controls. It may take the form of a revolving or fixed brush with bristles of appropriate stiffness, alone or in combination with an outlet jet. Any form of dislodgement system effective to disturb the pile of carpet fabrics, upholstery fabrics and the like so as to access the remote parts which might harbor bacterial spores or colonies can be used. This includes non-physical applications such as air jets, ultrasonic energy, radio-frequency energy and electromagnetic waves, for example, capable of causing physical disruption and which result in micro-physical movements of fibrous surfaces.

The ozone for use in the present invention can be generated by any known means. In the case of corona or other electrical discharge generation from oxygen, the apparatus of the invention preferably includes a container of medical grade oxygen. The oxygen container can be a standard, pressurized vessel containing medical grade oxygen, of the type commonly found in medical facilities. Oxygen from this container is fed to an ozone generator, where the oxygen is subjected to electrical discharge, normally with high voltage alternating current, to convert small amounts of the oxygen to ozone and produce a gaseous mixture of oxygen and ozone. The quantity of ozone in the mixture is controllable by adjustment of the voltage of the electrical discharge. Suitable ozone generators are known and available commercially. The relative amounts of ozone generated are relatively small, expressed in parts per million (ppm), but such is the power of ozone as a disinfectant, especially in combination with hydrogen peroxide in accordance with this invention, that such small quantities thereof are all that is required.

Alternative forms of ozone generation can be used if preferred. Ultraviolet radiation of appropriate short wavelength (non-biocidal), incident upon oxygen or air, is one acceptable alternative. In such a system, air from the room itself may be fed into the ozone generating unit to supply the required oxygen for conversion to ozone. Other methods of ozone generation which can be used include photocatalytic reactions, cold plasma, etc.

The relative humidity of the treatment space should be at least 60% and preferably at least 65%, for effective disinfection. To ensure this, it is preferred to incorporate a humidifier in the system of the invention, using sterile water from an internal system reservoir to adjust and control the humidity of the issuing gas mixture. In this way, desirable humidity at an appropriate droplet size for most effective disinfection is achieved at the point of discharge where dislodgement of a carpet or drapery surface can take place. The adjustable humidifier need only increase the humidity of the space to the desirable level and can be placed in any location within the space. When using hydrogen peroxide in addition to ozone, the hydrogen peroxide vapor is suitably applied, in controlled amounts, to the air/water vapor issuing from the humidifier and thus added to the ozone/oxygen containing gas mixture. Alternatively, hydrogen peroxide can be applied to the water used to humidify the target location. Hydrogen peroxide is commercially available as aqueous solutions of standard concentrations of hydrogen peroxide. For use in embodiments of the present invention, a standard solution of known peroxide concentration is suitably diluted down by a fixed volume of distilled water. The peroxide load is standardized based on the known volume of water from the peroxide solution required to raise the relative humidity to the desired extent, e.g. from 40-80%. From this, the amount of hydrogen peroxide in volume % or ppm by volume introduced into the treatment facility can be calculated.

Certain systems according to embodiments of the invention may include a temperature adjuster and controller for the gas mixture. This can be a simple heater/cooler through which either the incident oxygen or the generated oxygen/ozone/hydrogen peroxide mixture passes prior to discharge into the room atmosphere. While simple adjustment of the temperature of the room using an external room heating system and thermostat can be effective, it is preferred to adjust the temperature of the issuing gas mixture, for most effective treatment of the carpet and drapery surfaces. The ideal range of temperature for ozone and ozone/hydrogen peroxide decontamination of pathogens is 15° C. to 30° C.

The system of the invention also includes an ozone removal unit. Such units are known, and can be purchased commercially for use in the present invention. Depending on the volume of the room atmosphere and the capacity of the ozone removal unit, more than one such unit may be incorporated in the system of the invention. Suitable ozone removal units are those based on activated carbon as the removal medium. These act very quickly, and do not lead to the formation of hazardous reaction products. The inclusion of such units enables the treated facility to be cleared of ozone and returned to normal use rapidly, an important feature where health care facilities are involved. Other types include systems based on catalysts such as manganese oxide or other metal oxides, which may be heated to remove moisture, thermal destruction in conjunction with other metals including platinum or palladium.

FIG. 1 of the accompanying drawings shows a patient room surgical suite 10, closed ready for disinfection by a process according to an embodiment of the invention. The suite is substantially hermetically sealed. Inside the suite is a pressurized cylinder 12 of oxygen, feeding oxygen gas into a humidifier 14 and thence to an ozone generator 16, which includes electrical discharge plates of variable voltage to adjust the quantity of ozone which is generated. A heater and a pressure controller (not shown) may be disposed near the entrance to the ozone generator. Output of oxygen/ozone gas mixture is via room outlets 18, 20 to the atmosphere of the suite 10, and via wands 22A and/or 22B to a dislodgement means in the form of scrubbing brushes 24A and 24B mounted on the outlet ends of the respective wands 22A, 22B. The heater, the pressure controller, the voltage supplied to the ozone generator 16 and the humidity level supplied by the humidifier 14 are all controlled and adjusted from an external control panel 26 via respective electrical connections 28, 30, 32 and 34. Also disposed within the suite are an oscillating fan 34 and an ozone destruct filter unit 36.

Disposed within the suite 10 is a container of aqueous hydrogen peroxide solution 19 and associated air blower 21 which, during operation, blows vaporized hydrogen peroxide in controlled amounts into discharge wand 22A and 22B to mix with the output of ozone/oxygen therein. The amount of hydrogen peroxide being supplied is controlled by adjustment of the blower 21 through a connection thereof to the control panel 26. In an alternative arrangement, hydrogen peroxide can be supplied from generator 19 to the humidifier 14.

Figure 2A:
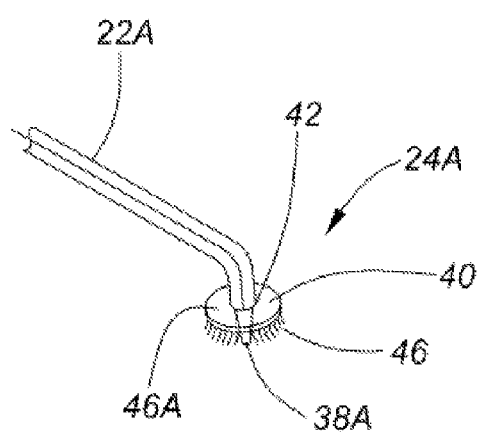
FIGS. 2A and 2B are diagrammatic illustrations of physical agitation systems for use in embodiments of the invention.
Figure 2B:
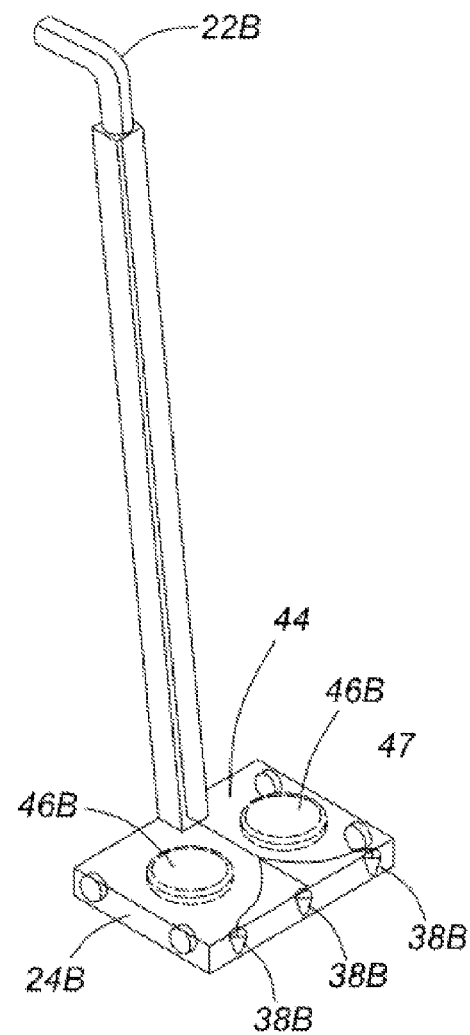

FIGS. 2A and 2B of the accompanying drawings show in more detail forms of dislodgement means 24A and 24B for use in the present invention, attached to the outlet, discharge ends of respective wands 22. The dislodgement means 24A has a jet outlet nozzle 38A at its extremity, and a generally circular plate 40 mounted on the wand 22A near the discharge end. The wand 22A passes through a central aperture 42 in a plate 40. The plate 40 has brush bristles 46A mounted on its lower surface, arranged in two arcs around the jet outlet nozzle 38A and protruding downwardly to an extent just beyond the extent of outlet from nozzle 38A. In use, oxygen/ozone gas mixture or oxygen/ozone/hydrogen peroxide gas mixture issues from nozzle 38A at relatively high pressure, and can be directed by the operator holding the wand to a carpet surface area while at the same time the operator scrubs the carpet surface area with the bristles 46A.

FIG. 2B shows an alternative but essentially similar arrangement, in which plate 40 is replaced by a wheeled platform 44 carrying two rotary brushes 46B and three jet outlets 38B for the oxygen/ozone/hydrogen peroxide delivery at pressure, located forwardly of the rotary brushes 46B.

Figure 3:
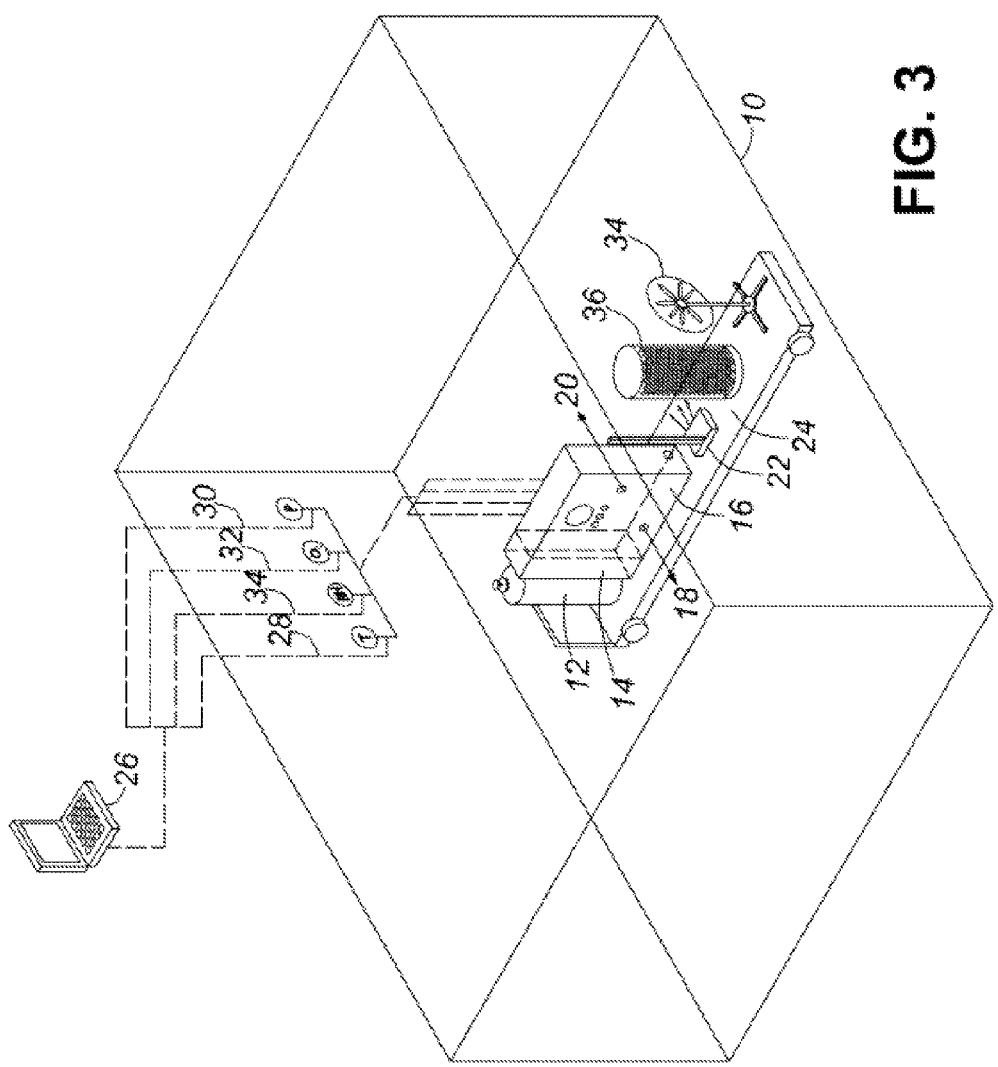
FIG. 3 is a diagrammatic illustration of an apparatus according to the invention, in portable, transportation mode.

FIG. 3 of the accompanying drawings illustrates the portability of a system according to the invention. Parts are numbered as in FIG. 1. A 4-wheeled cart 24 is provided, on which all the component parts of the system can be loaded for ease of transportation from one room to another. The instrumentation and control panel can be disconnected for transportation, and re-connected and disposed outside when the apparatus is placed in another room for use as shown in FIG. 1. The cart 24 is removed while the system is in use, but is loaded with the components after use, either for transportation to another room or for storage.

The operation of the system will be readily apparent from the preceding description of its component parts and their inter-connection. The cart 24 carrying the component parts is wheeled into the room 10 to be disinfected, and the parts are distributed around the room and connected together as illustrated in FIG. 1. An operator wearing a hazard suit and other appropriate protective clothing enters the room and holds the wand 22. The room is sealed. Conditions of treatment are set on the control panel 26, and the apparatus is switched on so that oxygen/ozone/hydrogen peroxide gas mixture at controlled ozone concentration, hydrogen peroxide concentration, relative humidity, temperature and elevated pressure issues from jet nozzle 38. The operator applies the jetted gas mixture to the carpet surfaces, drapery surfaces and other absorbent surfaces in the room, scrubbing the surfaces at the same time with the bristles 46. The room may be allowed to pressurize above atmospheric pressure by introduction of the oxygen/ozone/hydrogen peroxide gas mixture. If so, pressure is continually monitored by the control panel 26 to ensure safe working conditions for the operator, as well as the temperature, humidity and ozone/hydrogen peroxide concentrations in the room. Smooth surfaces in the room may not need the action of the dislodgement means, but are satisfactorily disinfected by contact with the atmosphere in the room containing hydrogen peroxide and ozone in combination. The oscillating fan 34 may be operated throughout or at intervals during the procedure, to circulate the oxygen/ozone/hydrogen peroxide mixture throughout the room. When operating the system at atmospheric pressure the fan preferably is operated only intermittently to permit periods when the application of force to the mixture is suspended, thereby to minimize movement of the mixture in the room in such periods so as to permit portions of the mixture in contact with bacteria to have extended contact with such bacteria.

After a pre-set time of the procedure, and after all the appropriate, absorbent surfaces have been scrubbed, a time not normally exceeding 90 minutes, the hydrogen peroxide supply, the oxygen supply and ozone generator are switched off. Then the ozone destruct filter is operated, sucking in the ozone-containing gases, destroying the ozone and issuing pure oxygen from it. Concurrently the room can be dehumidified thereby reducing the hydrogen peroxide levels to below 1.0 ppm. The room can now be opened, the apparatus disconnected and loaded on the cart 24, and the room put back to its normal use.

EXPERIMENTAL EXAMPLES

Figure 4:
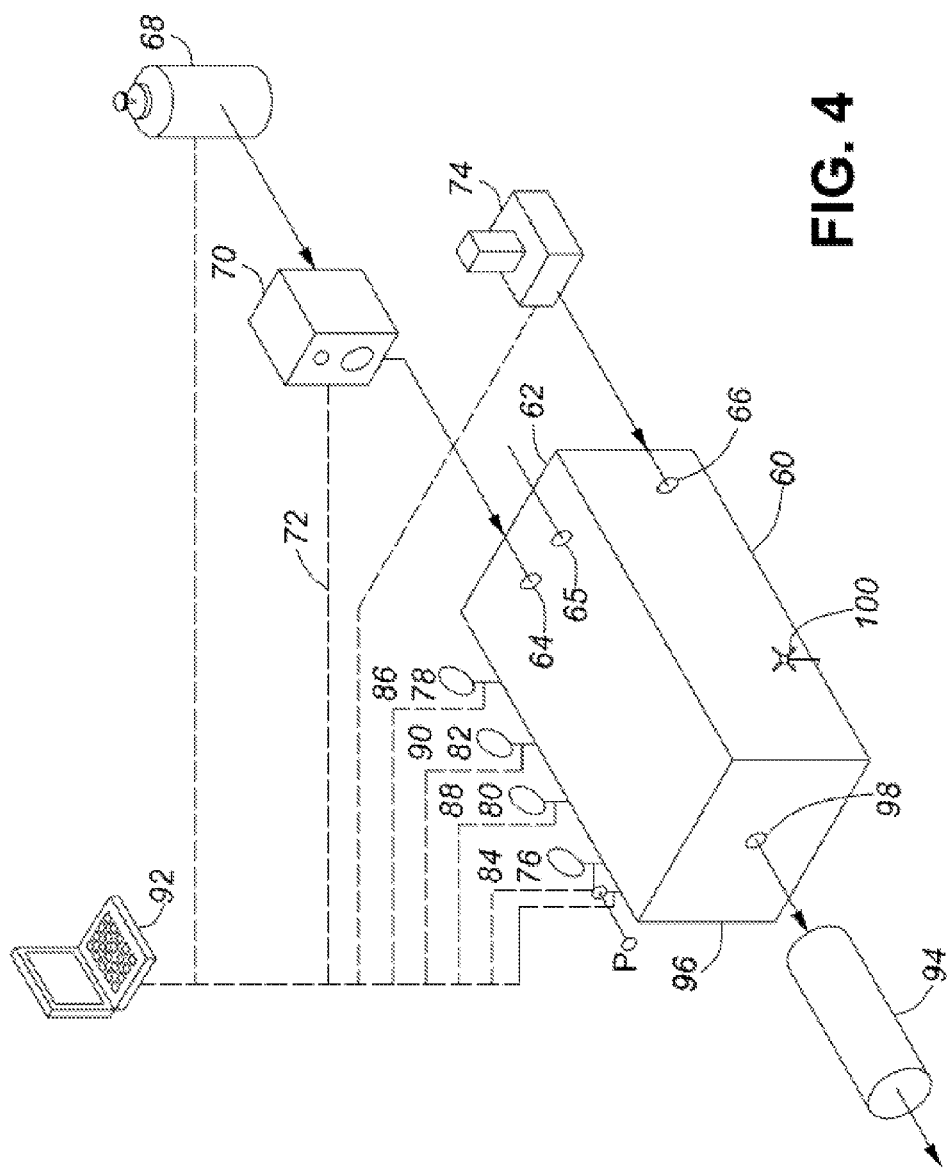
FIG. 4 is a diagrammatic illustration of a test apparatus used to generate some of the test results reported below.

Effective and optimum conditions for use in the present invention were determined using a laboratory apparatus as generally illustrated in FIG. 4 of the accompanying drawings.

A single pure colony of each aerobic test bacteria, namely *E. coli*; *Pseudomonas aeruginosa*; methicillin-resistant *Staphylococcus aureus* (MRSA); and vancomycin-resistant *Enterococcus* (VRE) was inoculated to a Columbia agar plate with 5% sheep's blood. They were incubated at 35° C. in room air for 18-24 hours. From the plate, 4-5 isolated colonies were selected, and suspended in tryptic soy broth to achieve a 0.5 McFarland turbidity standard ($1.5 \times 10^8$ cfu/ml) measured using a spectrophotometer. Inoculum was prepared by performing a series of serial dilutions of 0.9 ml 0.85 NaCl broth with 0.1 ml of original 0.5 McFarland inoculum ($6 \times 10$ fold) to give solutions of $10^{-1}$, $10^{-2}$, $10^{-3}$, $10^{-4}$, $10^{-5}$, $10^{-6}$ and $10^{-7}$ cfu/mL.

Organisms were plated out in triplicate, 0.1 ml of each solution being spread over the surface of Columbia sheep's blood agar plates. Two sets of plates (12 plates per organism) were subjected to ozone/oxygen exposure at preselected concentrations of ozone (ppm), humidity and temperature conditions in the illustrated apparatus. The other sets of 2 were treated as controls, with no ozone exposure, but kept at room temperature.

For ozone exposure, the apparatus generally illustrated in FIG. 4 was used.

The test plates were mounted inside a disinfection chamber 60, the upstream end 62 of which had an ozone inlet port 64, a hydrogen peroxide vapor inlet port 65 (which in Examples 1-9 described below was blocked), and a water vapor inlet port 66. A cylinder 68 of pressurized medical grade oxygen was provided, feeding oxygen to an ozone generator 70, equipped with alternating current electrical plates to which variable voltage could be supplied via input control 72. The output of oxygen/ozone mixed gas from the ozone generator 70 was fed to the ozone inlet port 64 of the disinfection chamber 60. A water vapor humidifier 74 supplied water vapor to inlet port 66. The disinfection chamber 60 also contained a heater/cooler (not shown), a temperature sensor 76, a pressure sensor 78, a humidity sensor 80 and an ozone sensor 82, connected electrically via respective lines 84, 86, 88 and 90 to a control panel and monitor 92, connected to feed back to the oxygen cylinder 68 to control flow for pressure adjustment purposes, to the ozone generator 70 to control and adjust the ozone quantity, to the water vapor humidifier 74 to control and adjust relative humidity in the disinfection chamber 60, and to the heater/cooler to control and adjust the temperature in the chamber. These parameters were all pre-set on the control panel to desired values and automatically re-adjusted themselves to these values as the experiments progressed.

An ozone destruct filter 94 was connected to the downstream end 96 of the disinfection chamber 60 at outlet port 98, to destroy ozone issuing from the chamber 60 at the end of the experiment. Gases were circulated within the chamber 60, and expelled therefrom at the termination of the experiment, using a fan 100 mounted therein. After placing the test plates in the chamber 60, it is sealed until the end of each experiment.

The control plates and the ozone treated plates were placed in an incubator at the same time. The plate counts were read through a microscope, and the numbers of colony forming units on each plate was counted. The spores are aerotolerant.

Example 1

A series of tests as described above was conducted on MRSA ATCC 33592. The microorganism-bearing dishes were exposed in the chamber to an oxygen/ozone mixed atmosphere containing 80 ppm ozone, for 90 minutes at 20° C. and 85% relative humidity. Duplicate test plates were run. 10 µL volume aliquots washed off the plates were serially diluted with inoculum, to final dilution factors $10^{-2}$, $10^{-3}$, $10^{-4}$, $10^{-5}$, $10^{-6}$ and $10^{-7}$. Control plates, not subjected to ozone exposure, were prepared, and the plates incubated for 24 hours as described. The surfaces of the agar plates were eluted to remove the bacterial colonies, and the eluates plated out for examination under a microscope.

Counting of the active, reproducing colonies of bacteria in the eluate compositions, under a microscope, revealed that the eluates from control plates at dilutions $10^{-2}$, had 19 and 11 cfus (duplicate plates), and no cfus from plates of higher dilution, whereas the experimental, ozone-exposed plates yielded compositions exhibiting no cfus at any of the tested dilutions. A 3.35 log reduction was achieved (8.3 log to 4.9 log).

Example 2

The experiment of example 1 was repeated using the same bacterial strain, but exposing the test plates in the chamber to 50 ppm ozone in oxygen, at 20° C. and 80% relative humidity.

Counting of the active, reproducing colonies of bacteria in the eluate compositions, under a microscope, revealed that the eluates from control plates at dilutions $10^{-2}$, had 374, 415, 414 and 423 cfus (quadruplicated plates), 33, 35, 38 and 37 cfus from control plates at dilutions $10^{-3}$, had 4, 1, 2 and 2 cfus at dilution $10^{-4}$ and no cfus at higher dilutions. Those from the eluates of treated plates revealed 27, 11, 42 and 58 active cfus at dilutions $10^{-2}$, 3, 1, 3 and 5 cfus at dilution $10^{-3}$ (quadruplicate plates), and no cfus from plates of higher dilution.

Example 3

The experiment of Example 1 was repeated, except for using as test organism *P. aeruginosa* ATCC 27853. The same conditions of ozone exposure, dilution, incubation and testing were used. On the test plates, active colony counts of 11 and 18 were found at $10^{-2}$ dilution, and active colony counts of 5 and 27 were found at $10^{-3}$ dilution. At higher dilutions, there were no detectable colonies. In contrast, the control, non-ozone exposed plates showed colonies too numerous to count, at all dilutions up to and including $10^{-6}$. A 2.8 log reduction was achieved (7.9 log to 5.1 log).

Example 4

The experiment of Example 3 was repeated, using the same test organism, but treating the test samples in the chamber with ozone/oxygen gas mixture containing 50 ppm ozone, at 80% humidity, for 90 minutes. By the same recovery and test procedures, it was determined that the control plates had cfus too numerous to count. The test plates, run in duplicate, had cfu counts of 212 and 183 at dilution $10^{-2}$; counts of 13 and 50 at dilution $10^{-3}$; and no cfus at higher dilutions.

Example 5

The experiment of Example 3 was repeated but using *Enterococcus faecalis* (high level vancomycin resistant) Clinical Strain 80269 as the test organism, with 90 minute exposure to ozone/oxygen mixture of 35 ppm ozone, at 21° C. and 80% relative humidity. The eluates from control plates (duplicated) had cfu counts too numerous to count at dilution $10^{-2}$, $10^{-3}$ and $10^{-4}$; cfu counts of 402 and 346 at dilution $10^{-5}$; cfu counts of 35 and 25 at dilution $10^{-6}$; and cfu counts of 14 and at dilution $10^{-7}$. In contrast, the eluates from the test plates (duplicates) gave cfu counts of 78 and 29 at dilution $10^{-2}$; cfu counts of 47 and 6 at dilution $10^{-3}$; 112 and 50 at dilution $10^{-4}$; cfu counts of 0 and 1 at dilution $10^{-5}$; cfu counts of 1 and 0 at dilution $10^{-6}$; and cfu counts of 0 and 1 at dilution $10^{-7}$. A 2.95 log reduction was achieved (7.7 log to 4.7 log).

Example 6

The experiment of Example 5 was repeated using the same VRE Clinical Strain as the test organism, but with 90 minute exposure to ozone/oxygen mixture of 50 ppm ozone, at 20° C. and 80% relative humidity. The eluates from control plates (duplicated) had cfu counts too numerous to count at dilution $10^{-2}$, $10^{-3}$ and $10^{-4}$; cfu counts of 369 and 359 at dilution $10^{-5}$; cfu counts of 46 and 46 at dilution $10^{-6}$; and cfu counts of 9 and 2 at dilution $10^{-7}$. In contrast, the eluates from the test plates (duplicates) gave cfu counts of 50 at dilution $10^{-2}$; cfu counts of less than 30 at dilution $10^{-3}$; and cfu counts of 0 at higher dilutions $10^{-5}$.

Example 7

The experiment of Example 3 was repeated but using *E. Coli* Strain ATCC 25922 as the test organism, with 90 minute exposure to ozone/oxygen mixture of 35 ppm ozone, at 21° C. and 80% relative humidity. The eluates from control plates (duplicated) had cfu counts too numerous to count at dilution $10^{-2}$, $10^{-3}$ and $10^{-4}$; cfu counts of greater than 300 at dilution $10^{-5}$; cfu counts of 95 and 66 at dilution $10^{-6}$; and cfu counts of 3 and 10 at dilution $10^{-7}$. In contrast, the eluates from the test plates (duplicates) gave cfu counts of 43 and 38 at dilution $10^{-2}$; cfu counts of 25 and 1 at dilution $10^{-3}$; 6 and 15 at dilution $10^{-4}$; cfu counts of 3 and 10 at dilution $10^{-5}$; and cfu counts of 0 at higher dilutions.

A 3.22 log reduction (7.8 log to 4.6 log) was achieved.

Example 8

The experiment of Example 7 was repeated was repeated using the same *E. Coli* Strain ATCC 25922 as the test organism, but with a 90 minute exposure to ozone/oxygen mixture of 50 ppm ozone, at 20° C. and 80% relative humidity. The eluates from control plates (duplicated) had cfu counts too numerous to count at dilution $10^{-2}$, $10^{-3}$ and $10^{-4}$; cfu counts of 563 and 350 at dilution $10^{-5}$; cfu counts of 74 and 87 at dilution $10^{-6}$; and cfu counts of 7 and 7 at dilution $10^{-7}$. In contrast, the eluates from the test plates (duplicates) gave cfu counts of 13 and 28 at dilution $10^{-2}$; cfu counts of 8 and 7 at dilution $10^{-3}$; cfu counts of 7 and 5 at dilution $10^{-4}$; and 0 at all other, higher dilutions.

Example 9

A strain of *C. difficile* (clinical strain nontoxigenic #135, Queens University Medical School, Kingston, Ontario, Canada) was also used as a test organism, but owing to the well-known difficulties with growing *C. difficile* strains (anaerobic condition requirements, for example), a somewhat different preparatory method was adopted.

The *C. difficile* strain was streaked on 12-20 pre-reduced *Brucella* blood agar plates and incubated anaerobically for 48 hours at 35° C. Each plate was flooded with 5 ml of sterile distilled water and the bacterial colonies gently scraped from the agar surface with a plastic sterile bacteriological loop. The resulting bacterial suspension was mixed and allowed to rest at room temperature in a sealed tube for 20 minutes to permit the osmotic lysis of the vegetative forms of the bacteria. The bacterial suspension was centrifuged at 3,000× gravity for 20 minutes to pellet the spores and remaining bacterial cells. The supernatant was discarded and the pellet re-suspended in 5-7 milliliters of sterile distilled water and mixed vigorously to re-suspend the spores and remaining bacterial cells. The above steps were repeated three times to produce a pellet consisting of C. difficile spores. To kill any remaining vegetative bacteria, the final suspension was placed in a heating block at 70° C. for 20 minutes. The spores were stored in 100% ethanol at 4° C. This preparation yielded approximately $1.5 \times 10^5$ cfu/ml of spores. Gram stain of the spore preparation confirmed that the suspension consists of spores with very few vegetative cells.

Serial 10 fold dilutions of the spore suspension in sterile 0.85% NaCl were conducted as previously described, and then inoculation was conducted by spreading 0.1 ml of each dilution over the surface of BAK agar plates. The yield of C. difficile spores was about $6 \times 10^4$–$2 \times 10^6$ cfu/ml. Some plates were exposed to ozone in the illustrated apparatus as previously described, others were kept as controls.

Test plates were given a 90 minute exposure to ozone/oxygen mixture of 35 ppm ozone, at 21° C. and 80% relative humidity. The subsequent incubation was for 48 hours under anaerobic conditions. The eluates from control plates (duplicated) had cfu counts of 113 and 50 at dilution $10^{-2}$ and 10 and 10 at dilution $10^{-3}$; whereas the eluates from the test plates showed no cfus at any dilution tested.

A 4 log reduction (4 log to zero) was achieved.

Example 10

Figure 5:
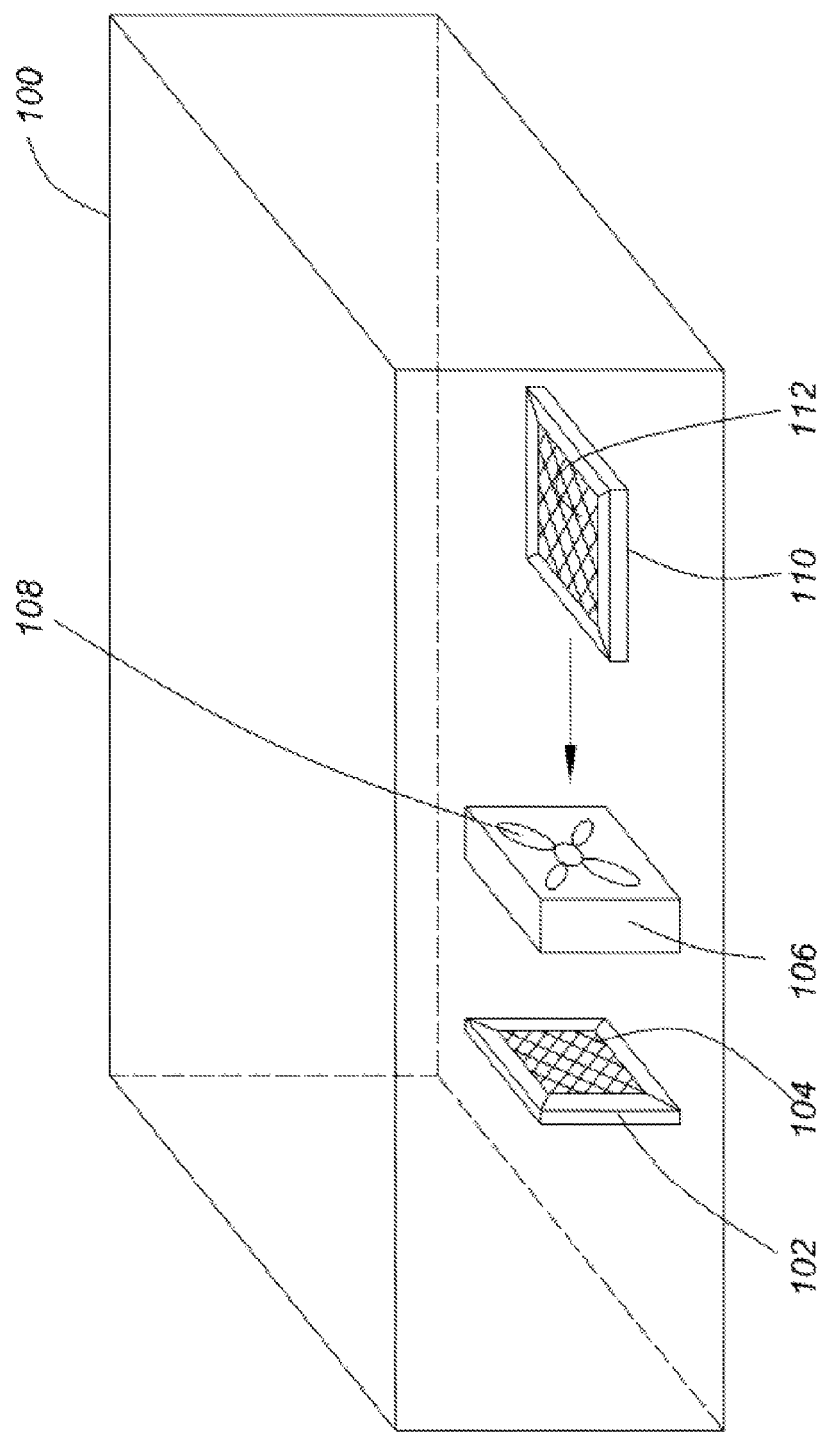
FIG. 5 is a diagrammatic illustration of the test apparatus used to generate the results reported in Example 10 below.

Experiments conducted to simulate the problems commonly faced in most modern hospitals related to decontaminating textiles such as carpets and drapes have clearly demonstrated the superior efficacy of direct pressurized air flow over a more static gaseous environment. An apparatus as diagrammatically illustrated in the accompanying FIG. 5 was used. A chamber 100, closed while the experiments were in progress, contained near one end a frame 102 holding a layer (disc) 104 of fibrous drape material (sterile cotton gauze), impregnated with MRSA and dried so that a biofilm formed. Ozone rich atmosphere is fed into the chamber. An electrical fan 106 with rotary blades 108 was disposed 3 cm from the gauze, so as to blow gases within the chamber through the gauze at high velocity, to cause physical agitation of the gauze. A dish 110 containing an exposed, similarly impregnated gauze 112 was disposed near the other end of the chamber 100, so that it was exposed to essentially static atmosphere in the chamber. A control gauze, which was similarly impregnated but received no treatment, was also evaluated.

The results are reported in Table 1 below. In Table 1, columns A, B, C and D are the results at 10 fold serial dilutions, obtained by standard procedure. Results measured on gauzes subjected to physical agitation are recorded as "direct". Those on the gauzes in essentially static atmosphere are recorded as "indirect".

In all instances, the combination of 80 ppm ozone and 1% $H_2O_2$ at a relative humidity of 80% with an exposure time of 30 minutes proved superior to all other combinations including 1% $H_2O_2$ with no ozone and 80 ppm ozone with no $H_2O_2$. In these experiments the methodology utilized with respect to microbiological procedures was the same as that described above for other experiments. Accordingly it has been concluded that in order to achieve a 6-7 log bacterial kill in hospital environments wherein carpets and other textiles are commonly found, an ozone/$H_2O_2$ pressure applicator or physical agitator is essential. Based on the experiments provided and other research, the incremental improvement in bacterial kill achievable through a pressure applicator is in the order of 2-3 logs (100-1000× greater).

TABLE 1

| A Run # | B Organism | C Ozone (PPM) | D H2O2 (%) | E EXP (min) | F Humidity | G Disc | H A | I B | J C | K D | L |
|---|---|---|---|---|---|---|---|---|---|---|---|
| Control | MRSA | 0 | 0 | 0 | 0 | Control | TNTC | 180 | 2 | 0 | |
| 1 | MRSA | 80 | 1 | 30 | 80 | 1 | 0 | 0 | 0 | 0 | Direct |
| 2 | MRSA | 80 | 1 | 30 | 80 | 2 | 77 | 11 | 2 | 1 | Indirect |
| 3 | MRSA | 0 | 0 | 60 | 80 | 3 | TNTC | TNTC | 181 | 12 | Direct |
| 4 | MRSA | 0 | 0 | 60 | 80 | 4 | TNTC | 233 | 21 | 3 | Indirect |
| 5 | MRSA | 0 | 1 | 60 | 80 | 5 | 220 | 34 | 0 | 0 | Direct |
| 6 | MRSA | 0 | 1 | 60 | 80 | 6 | 245 | 112 | 0 | 0 | Indirect |
| 7 | MRSA | 0 | 1 | 90 | 80 | 7 | 134 | 10 | 2 | 0 | Direct |
| 8 | MRSA | 0 | 1 | 90 | 80 | 8 | 112 | 17 | 3 | 0 | Indirect |
| 9 | MRSA | 80 | 0 | 30 | 80 | 9 | 43 | 14 | 0 | 0 | Direct |
| 10 | MRSA | 80 | 0 | 30 | 80 | 10 | 112 | 15 | 3 | 0 | Indirect |
| 11 | MRSA | 0 | 1 | 90 | 80 | 11 | 86 | 12 | 0 | 0 | Direct |
| 12 | MRSA | 0 | 1 | 90 | 80 | 12 | 136 | 54 | 0 | 0 | Indirect |

Example 11

Test bacteria, namely Clostridium difficile (C. difficile); E. coli; Pseudomonas aeruginosa (PAU); methicillin-resistant Staphylococcus aureus (MRSA); vancomycin-resistant Enterococcus (VRE); were prepared as described for the previous experiments (see Example 1 for the preparation of the aerobic bacteria, Example 9 for the preparation of C. difficile). Bacillus subtilis (the surrogate for anthrax) was prepared analogously to the preparation of C. difficile, except that the bacteria was grown on Columbia sheep's blood agar plates incubated for 18-24 hours in room air at 35° C. They were separately cultured on plates for 24 hours. From the plate, 4-5 isolated colonies were selected, and suspended in 0.85 NaCl to achieve a 0.5 McFarland turbidity standard ($1.5 \times 10^8$ cfu/ml) measured using a spectrophotometer. Inoculum was prepared by performing a series of serial dilutions of 0.9 ml 0.85 NaCl broth with 0.1 ml of original 0.5 McFarland inoculum (6×10 fold) to give solutions of $10^{-1}$, $10^{-2}$, $10^{-3}$, $10^{-4}$, $10^{-5}$, $10^{-6}$ and $10^{-7}$ cfu/mL. Organisms were plated out in triplicate, as previously described, 0.1 ml of each solution being spread over the surface of Columbia sheep's blood agar (in respect of the aerobic bacteria) or Brucella anaerobic blood agar plates (in respect of C. difficile and B. subtilis) on plates, or on stainless steel plates. On agar, the bacteria maintain planktonic mode. On steel plates, biofilms containing the bacteria form.

For the experiments on steel plates, 40 microliters of the original inoculum as prepared above was placed onto the surface of a series of 1 cm diameter stainless steel discs. These were allowed to dry in a biological safety cabinet for approximately 45 minutes until the inoculum spots were dry. The steel discs were placed in a sterile Petri dish to facilitate their transfer to the test chamber. Once dry, the lid of the Petri dish was placed over the discs, and they were carefully transferred to the treatment location where they were exposed to the ozone test conditions. Appropriate numbers of control discs are left covered in the biological safety cabinet, and not exposed to the ozone test conditions.

Some of the plates were subjected to ozone/oxygen exposure using ozone 80 ppm, 42-80% humidity and room temperature of about 22° C., for a period of 90 minutes, in the illustrated apparatus, as controls. Additional controls had no ozone or hydrogen peroxide treatment, but were prepared and exposed in the same way.

With reference to FIG. 4, the test plates were mounted inside the disinfection chamber 60, and treated with ozone and water vapor as previously described, but additionally using hydrogen peroxide supplied as a vapor to the chamber via port 65. The disinfection chamber 60 also contained the same heater/cooler system and sensors previously described.

Plates treated according to the invention were exposed to 80 ppm ozone and gaseous hydrogen peroxide from a 1% or a 3% aqueous solution, air being blown through the aqueous solution in the illustrated apparatus to create the gaseous hydrogen peroxide. Other conditions and exposure times were kept the same.

Immediately after the exposure to the test conditions, and similarly for the unexposed control discs, the stainless steel discs were vigorously mixed in 10 ml of sterile 0.85% saline using a vortex mixer at high speed for 60 seconds to elute off all surviving viable bacteria or spores. The eluted suspension, containing both living and dead bacteria, is serially diluted 10 fold in sterile 0.85% saline and the diluted bacteria were quantitatively plated onto Columbia sheep's blood agar plates for the aerobic bacteria or *Brucella* anaerobic blood agar plates for *C. difficile*, incubated under appropriate conditions, in triplicate so as to determine the original inoculum concentration. The survivor colony counts were logarithmically transformed and the geometric mean calculated. The difference between the bacterial counts of the unexposed controls and the exposed test discs yielded the logarithmic reduction in bacteria under the test conditions. If this procedure results in no growth, 100% of the bacteria within the biofilm have been killed by exposure to the ozone/hydrogen peroxide.

The agar plates after exposure were cultivated in an incubator for 24 hours. The plates were then stained, examined through a microscope, and the numbers of colony forming units on each plate was counted.

The results are reported in Table 2 below, as 10 fold reductions in live bacteria on the agar plate or the steel plate, in comparison with the starting plate prior to any exposure. Thus a value of 1 means a 10 fold or one log reduction relative to the control samples which is not considered a significant effect. A value of 5 means a 5 log or 99.999% reduction in live bacteria was achieved, enough to be termed "full disinfection", for practical purposes. A value of 6 means a 6 log or 99.9999% reduction in live bacteria was achieved which is defined internationally as (CDC) as "sterilization". The bacterial strains were as reported in the previous experiments. The *Bacillus subtilis* was ATCC 19659 spores.

TABLE 2

| Bacteria | Ozone 80 ppm alone Agar | Ozone 80 ppm alone Steel | $H_2O_2$ 3% alone agar | $H_2O_2$ 3% alone steel | Ozone 80 ppm + 1% $H_2O_2$ steel |
|---|---|---|---|---|---|
| C. difficile | 4.5 | 2.5-3.0 | 1.5 | 1.00 | 6.5+ |
| MRSA | 4.5 | 5.0 | 1.5 | 1.5 | 7.0+ |
| E. Coli | 4.0 | 3.5 | 2.0 | 1.0 | 7.0 |
| VRE | 4.5 | 3.5 | 1.0 | 1.0 | 6.5 |
| PAU | 4.0 | 3.0 | 2.0 | 0.5 | 7.0 |
| Bacillus Sub | | | 1.0 | 1.0 | 7.0+ |

Example 12

Tables 3, 4, 5, 6, 7 and 8 below provide a summary of experiments, whereby combinations of ozone, $H_2O_2$, humidity and exposure time were evaluated in terms of the ability to eliminate the following bacteria when artificially applied as a biofilm onto non-porous surfaces such as stainless steel discs: *E. coli; Pseudomonas aeruginosa* (PAU); *Bacillus subtilis* (the surrogate for anthrax). *Clostridium difficile* (*C. difficile*); vancomycin-resistant *Enterococcus* (VRE); and methicillin-resistant *Staphylococcus aureus* (MRSA), same strains as before.

The steel discs for testing and the agar plates for testing were prepared exposed and tested as described in the previous example, with exposure conditions shown in the Tables below. In some cases, indicated as "chamber", the tests were conducted as described in Example 10 and with an apparatus generally as illustrated in FIG. 4. In other cases indicated as "room", the tests were conducted by exposing the disks and plates in a closed room, as generally illustrated in FIG. 1.

The below Tables of results also report a period of post exposure (PEEP), in minutes, which is the time interval between the ozone/peroxide exposure termination and the start of the procedure for determining the results. This simulates real practice in disinfecting hospital rooms and similar environments, where bacteria, after disinfectant treatment, die over a period of time. To allow for this, it is preferred that at least 25 minutes should elapse from the time the ozone/hydrogen peroxide exposure terminates before the disinfected room is put back into normal service.

TABLE 3

E. Coli

| | B | C | D | E | F | G | H | I |
|---|---|---|---|---|---|---|---|---|
| 1 | | | | *Escherichia coli* - ATCC | | | | |
| 2 | Material | O3 (PPM) | $H_2O_2$ % | % Humidity | Exp | PEEP | Cham./Room | Log10 RED |
| 3 | Steel | 80 | 1 | 80-85 | 90 | 90 | Chamber | 5.99 |
| 4 | Steel | 80 | 1 | 80-85 | 60 | 90 | Chamber | 5.99 |
| 5 | Steel | 80 | 1 | 80-85 | 45 | 90 | Chamber | 5.99 |
| 6 | Steel | 80 | 1 | 80-85 | 45 | 0 | Chamber | 5.99 |
| 7 | Steel | 80 | 1 | 80-85 | 60 | 0 | Room | 6.02 |
| 8 | Steel | 80 | 1 | 80-85 | 25 | 0 | Chamber | 6.8 |
| 9 | Steel | 80 | 1 | 80-85 | 35 | 0 | Chamber | 6.8 |
| 10 | Steel | 80 | 1 | 80-85 | 45 | 0 | Chamber | 6.8 |
| 11 | Steel | 80 | 1 | 80-85 | 60 | 0 | Chamber | 6.8 |
| 3 | Steel | 80 | 1 | 80-85 | 90 | 90 | Chamber | 5.01 |
| 4 | Steel | 80 | 1 | 80-85 | 90 | 90 | Chamber | 5.01 |
| 5 | Steel | 80 | 1 | 80-85 | 90 | 90 | Chamber | 5.01 |
| 6 | Steel | 80 | 1 | 80-85 | 25 | 0 | Chamber | 7.36 |
| 7 | Steel | 80 | 1 | 80-85 | 35 | 0 | Chamber | 7.36 |
| 8 | Steel | 80 | 1 | 80-85 | 45 | 0 | Chamber | 7.36 |
| 9 | Steel | 80 | 1 | 80-85 | 60 | 0 | Chamber | 7.36 |
| 10 | Steel | 80 | 1 | 80-85 | 45 | 0 | Chamber | 6.35 |

TABLE 3-continued

*E. Coli*

*Escherichia coli* - ATCC

| | Material | O3 (PPM) | H₂O₂ % | % Humidity | Exp | PEEP | Cham./Room | Log10 RED |
|---|---|---|---|---|---|---|---|---|
| 11 | Steel | 80 | 1 | 80-85 | 60 | 0 | Chamber | 6.35 |
| 12 | Steel | 80 | 1 | 80-85 | 90 | 0 | Chamber | 6.35 |

Table 4-Pseudo

TABLE 5

*Bacillus Subtilus*

*Bacillus subtilis*

| | Material | O3 (PPM) | H2O2 % | Humidity % | Exp. | PEEP | Cham./Room | Log-10 RED |
|---|---|---|---|---|---|---|---|---|
| 3 | Steel | 80 | 0.5 | 80-85 | 90 | 90 | Chamber | 0.5 |
| 4 | Steel | 80 | 1 | 80-85 | 90 | 0 | Chamber | 0.1 |
| 5 | Steel | 80 | 3 | 80-85 | 90 | 0 | Chamber | 7.23 |
| 6 | Steel | 0 | 3 | 80-85 | 90 | 90 | Chamber | 0 |
| 7 | Steel | 80 | 3 | 80-85 | 90 | 90 | Chamber | 7.23 |
| 8 | Steel | 80 | 1 | 80-85 | 90 | 90 | Chamber | 7.23 |
| 9 | Steel | 80 | 1 | 80-85 | 90 | 90 | Chamber | 4.61 |
| 10 | Steel | 80 | 1 | 80-85 | 90 | 90 | Chamber | 4.61 |
| 11 | Steel | 80 | 1 | 80-85 | 90 | 90 | Chamber | 4.61 |
| 12 | Steel | 80 | 1 | 80-85 | 90 | 90 | Room | 6.6 |
| 13 | Steel | 80 | 3 | 80-85 | 90 | 90 | Room | 6.6 |
| 14 | Steel | 80 | 3 | 80-85 | 90 | 0 | Room | 6.6 |
| 15 | Steel | 80 | 1 | 80-85 | 90 | 90 | Chamber | 6.34 |
| 16 | Steel | 80 | 3 | 80-85 | 90 | 90 | Chamber | 6.34 |
| 17 | Steel | 80 | 3 | 80-85 | 90 | 0 | Chamber | 6.34 |

TABLE 6

*C. Diff*

*Clostridium Difficile* - ATCC

| | Material | O3 (PPM) | H2O2 % | Humidity % | Exp. | PEEP | Cham./Room | Log-10 RED |
|---|---|---|---|---|---|---|---|---|
| 3 | Steel | >1000 | 0 | 87 | 90 | 90 | Chamber | 3.734 |
| 4 | Steel | 80 | 0 | 87 | 90 | 90 | Chamber | 3.135 |
| 5 | Steel | 180 | 0 | 87 | 45 | 90 | Chamber | 3.161 |
| 6 | Steel | 80 | 0 | 87 | 90 | 90 | Chamber | 2.76 |
| 7 | Steel | 180 | 0 | 87 | 90 | 90 | Chamber | 2.96 |
| 8 | Steel | 80 | 0 | 87 | 90 | 90 | Chamber | 1.95 |
| 9 | Steel | 180 | 0 | 87 | 90 | 90 | Chamber | 1.47 |
| 10 | Steel | 80 | 1 | 80-85 | 90 | 90 | Chamber | UNK |
| 11 | Steel | 80 | 3 | 80-85 | 90 | 90 | Chamber | 6.23 |
| 12 | Steel | 80 | 0.5 | 80-85 | 90 | 0 | Chamber | 6.23 |
| 13 | Steel | 50 | 0.5 | 80-85 | 90 | 90 | Chamber | UNK |
| 14 | Steel | 50 | 3 | 80-85 | 90 | 90 | Chamber | 1.29 |
| 15 | Steel | 80 | 0.5 | 80-85 | 90 | 90 | Chamber | 6.72 |
| 16 | Steel | 80 | 1 | 80-85 | 90 | 90 | Room | 5.75 |
| 17 | Steel | 80 | 1 | 80-85 | 45 | 0 | Chamber | 7.9 |
| 18 | Steel | 80 | 1 | 80-85 | 60 | 0 | Chamber | 7.9 |
| 19 | Steel | 80 | 1 | 80-85 | 90 | 0 | Chamber | 7.9 |

TABLE 7

VRE

Vancomycin Resistant Enterococcus - ATCC

| | Material | O3 (PPM) | H2O2 % | Humidity % | Exp. | PEEP | Cham./Room | Log-10 RED |
|---|---|---|---|---|---|---|---|---|
| 3 | Steel | 400 | 0 | 80 | 90 | 90 | Chamber | 1.19 |
| 4 | Steel | 80 | 0 | 80 | 90 | 90 | Chamber | 0.66 |
| 5 | Steel | 80 | 0 | 65 | 90 | 90 | Chamber | 1.44 |
| 6 | Steel | 130 | 0 | 65 | 90 | 90 | Chamber | 0.22 |
| 7 | Steel | 130 | 0 | 65 | 90 | 90 | Chamber | 1.08 |
| 8 | Steel | 80 | 1 | 80-85 | 90 | 90 | Chamber | 5.74 |
| 9 | Steel | 80 | 1 | 80-85 | 90 | 90 | Chamber | 5.74 |
| 10 | Steel | 80 | 1 | 80-85 | 90 | 90 | Chamber | 5.74 |
| 11 | Steel | 80 | 1 | 80-85 | 90 | 90 | Room | 5.96 |
| 12 | Steel | 80 | 1 | 80-85 | 60 | 90 | Room | 5.96 |
| 13 | Steel | 80 | 1 | 80-85 | 45 | 90 | Room | 5.96 |
| 14 | Steel | 80 | 1 | 80-85 | 45 | 0 | Room | 5.96 |
| 15 | Steel | 80 | 1 | 80-85 | 60 | 0 | Chamber | 6.08 |
| 16 | Steel | 80 | 1 | 80-85 | 25 | 0 | Chamber | 5.8 |
| 17 | Steel | 80 | 1 | 80-85 | 35 | 0 | Chamber | 5.8 |
| 18 | Steel | 80 | 1 | 80-85 | 45 | 0 | Chamber | 5.8 |
| 19 | Steel | 80 | 1 | 80-85 | 60 | 0 | Chamber | 5.8 |

TABLE 8

MRSA

MRSA - ATCC 33952

| | Material | O3 (PPM) | H2O2 % | Humidity % | Exp. | PEEP | Cham./Room | Log-10 RED |
|---|---|---|---|---|---|---|---|---|
| 3 | Steel | 400 | 0 | 80 | 90 | 90 | Chamber | 1.223 |
| 4 | Steel | 80 | 0 | 80 | 90 | 90 | Chamber | 0.83 |
| 5 | Steel | 80 | 0 | 65 | 90 | 90 | Chamber | 1.44 |
| 6 | Steel | 130 | 0 | 65 | 90 | 90 | Chamber | 0.22 |
| 7 | Steel | 130 | 0 | 65 | 90 | 90 | Chamber | 1.08 |
| 8 | Agar | >1000 | 0 | 80 | 90 | 90 | Chamber | 5.15 |
| 9 | Agar | 80 | 0 | 80 | 90 | 90 | Chamber | 4.899 |
| 10 | Agar | 130 | 0 | ? | 90 | 90 | Chamber | 4.695 |
| 11 | Steel | 80 | 0 | 60-70 | 90 | 90 | Chamber | 0.49 |
| 12 | Steel | 180 | 0 | 80 | 90 | 90 | Chamber | 0.66 |
| 13 | Steel | 500 | 0 | 80 | 90 | 90 | Chamber | 6.73 |
| 14 | Steel | 180 | 0 | 80-85 | 90 | 0 | Chamber | 0.99 |
| 15 | Steel | 180 | 0 | 80-85 | 90 | 90 | Chamber | 6.23 |
| 16 | Steel | 500 | 0 | 80-85 | 90 | 90 | Chamber | 6.23 |
| 17 | Steel | 50 | 0 | 80-85 | 90 | 0 | Chamber | 0.97 |
| 18 | Steel | 50 | 0 | 80-85 | 90 | 90 | Chamber | 1.03 |
| 19 | Steel | 80 | 0 | 80-85 | 90 | 0 | Chamber | 1.04 |
| 20 | Steel | 80 | 0 | 80-85 | 90 | 90 | Chamber | 1.52 |
| 21 | Steel | 120 | 0 | 80-85 | 90 | 0 | Chamber | 0.81 |
| 22 | Steel | 120 | 0 | 80-85 | 90 | 90 | Chamber | 0.99 |
| 23 | Steel | 180 | 0 | 80-85 | 90 | 0 | Chamber | 0.62 |
| 24 | Steel | 180 | 0 | 80-85 | 90 | 90 | Chamber | 1.51-6.5? |
| 25 | Steel | 80 | 0 | 80-85 | 90 | 90 | Chamber | 1.32-6.53 |
| 26 | Steel | 80 | 3 | 80-85 | 90 | 90 | Chamber | 6.53 |
| 27 | Steel | 180 | 3 | 80-85 | 90 | 90 | Chamber | 6.53 |
| 28 | Steel | 80 | 0 | 80-85 | 90 | 90 | Chamber | 0.51 |
| 29 | Steel | 80 | 1 | 80-85 | 90 | 90 | Chamber | 6.39 |
| 30 | Steel | 0 | 1 | 80-85 | 90 | 90 | Chamber | 0.13 |
| 31 | Steel | 30 | 1 | 80-85 | 90 | 90 | Chamber | 1.32 |
| 32 | Steel | 80 | 0.5 | 80-85 | 90 | 0 | Chamber | 6.43 |
| 33 | Steel | 80 | 1 | 80-85 | 90 | 0 | Room | 6.43 |
| 34 | Steel | 80 | 1 | 80-85 | 90 | 0 | Room | 6.36 |
| 35 | Steel | 80 | 3 | 80-85 | 60 | 90 | Room | 6.36 |
| 36 | Steel | 80 | 3 | 80-85 | 45 | 0 | Room | 6.36 |
| 37 | Steel | 80 | 1 | 80-85 | 90 | 90 | Chamber | 6.6 |
| 38 | Steel | 80 | 3 | 80-85 | 90 | 90 | Chamber | 6.6 |

TABLE 8-continued

MRSA

| 1 | B | C | D | E | F | G | H | I |
|---|---|---|---|---|---|---|---|---|
|   |   |   | MRSA - ATCC 33952 |   |   |   |   |   |
| 2 | Material | O3 (PPM) | H2O2 % | Humidity % | Exp. | PEEP | Cham./Room | Log-10 RED |
| 39 | Steel | 80 | 3 | 80-85 | 90 | 0 | Chamber | 6.6 |
| 40 | Steel | 80 | 1 | 80-85 | 25 | 0 | Chamber | 6.7 |
| 41 | Steel | 80 | 1 | 80-85 | 35 | 0 | Chamber | 6.7 |
| 42 | Steel | 80 | 1 | 80-85 | 45 | 0 | Chamber | 6.7 |
| 43 | Steel | 80 | 1 | 80-85 | 60 | 0 | Chamber | 6.7 |
| 44 | Steel | 80 | 1 | 80-85 | 45 | 0 | Chamber | 8.11 |
| 45 | Steel | 80 | 1 | 80-85 | 60 | 0 | Chamber | 8.11 |
| 46 | Steel | 80 | 1 | 80-85 | 90 | 0 | Chamber | 8.11 |
| 47 | Steel | 80 | 0.2 | 45 | 30 | 0 | Chamber | 0.128 |
| 48 | Steel | 80 | 0.2 | 45 | 60 | 0 | Chamber | 1.169 |
| 49 | Steel | 80 | 0.2 | 45 | 90 | 0 | Chamber | 1.29 |
| 50 | Steel | 80 | 0.2 | 60 | 30 | 0 | Chamber | 0.04 |
| 51 | Steel | 80 | 0.2 | 60 | 60 | 0 | Chamber | 0.987 |
| 52 | Steel | 80 | 0.2 | 60 | 90 | 0 | Chamber | 1.86 |
| 53 | Steel | 80 | 0.2 | 80 | 30 | 0 | Chamber | 1.4 |
| 54 | Steel | 80 | 0.2 | 80 | 60 | 0 | Chamber | 2.4 |
| 55 | Steel | 80 | 0.2 | 80 | 90 | 0 | Chamber | 8.452 |
| 56 | Steel | 80 | 1 | 60 | 30 | 0 | Chamber | 1.049 |
| 57 | Steel | 80 | 1 | 60 | 60 | 0 | Chamber | 2.505 |
| 58 | Steel | 80 | 1 | 60 | 90 | 0 | Chamber | 8.452 |
| 59 | Steel | 80 | 1 | 80 | 30 | 0 | Chamber | 7.37 |
| 60 | Steel | 80 | 1 | 80 | 60 | 0 | Chamber | 7.37 |
| 61 | Steel | 80 | 1 | 80 | 90 | 0 | Chamber | 7.37 |
| 62 | Steel | 80 | 3 | 45 | 30 | 0 | Chamber | 0.849 |
| 63 | Steel | 80 | 3 | 45 | 60 | 0 | Chamber | 2.57 |
| 64 | Steel | 80 | 3 | 45 | 90 | 0 | Chamber | 8.086 |
| 65 | Steel | 80 | 3 | 60 | 30 | 0 | Chamber | 1.87 |
| 66 | Steel | 80 | 3 | 60 | 90 | 0 | Chamber | 8.086 |
| 67 | Steel | 80 | 3 | 80 | 30 | 0 | Chamber | 7.37 |
| 68 | Steel | 80 | 3 | 80 | 60 | 0 | Chamber | 7.37 |
| 69 | Steel | 80 | 3 | 80 | 90 | 0 | Chamber | 7.37 |

The findings with respect to *Bacillus subtilis* clearly indicate that 80 ppm ozone, 1% $H_2O_2$ at 80% relative humidity produces a 6 log(+) reduction when these aerobic spores are exposed for 90 minutes. Given the uniqueness of this bacteria and the fact that it is routinely used as a surrogate for anthrax, the above combination of treatment parameters renders this device highly effective in a bioterrorism countermeasures scenario.

The findings with respect to *Pseudomonas aeruginosa* show definitely that 80 ppm ozone, 1% $H_2O_2$ at 80% relative humidity with an exposure time of 25 minutes produces a 100% kill (7+ logs). The same findings were observed when biofilms of *E. coli* samples on stainless steel discs were exposed for 25 minutes to a combination of 80 ppm ozone, 1% $H_2O_2$ at a relative humidity of 80%.

With respect to *Clostridium difficile* and vancomycin resistant *Enterococcus*, the same combination of 80 ppm ozone, 1% $H_2O_2$ and 80% relative humidity proved highly effective in achieving 100% elimination of bacteria in biofilms placed on a stainless steel surface and exposed for 45 minutes.

The results summarized in Table 8 above clearly demonstrates that the same combination of 80 ppm ozone, 1% $H_2O_2$ and 80% relative humidity achieves 100% kill (6+ log reduction) when biofilms of MRSA were exposed for 30 minutes.

Example 13

Test runs were conducted in order to determine the effects of variations in the application of force to, and consequent movement of a disinfecting atmosphere, i.e. through agitation of the disinfecting atmosphere by operation of a fan in a treated room, on the kill effectiveness of the ozone/hydrogen peroxide mixture during a 30 minute treatment in the room at atmospheric pressure in accordance with the invention. The results are as follows:

| Air Current Strength | Ozone Concentration | $H_2O_2$ Concentration | Exposure Time | Pathogen | Log Reduction |
|---|---|---|---|---|---|
| No air current | 80 ppm | 1.0% | 30 mins. | MRSA | 6.4 logs |
|  |  |  |  | VRE | 6.9 logs |
| Low Fan = #1 | 80 ppm | 1.0% | 30 mins. | MRSA | 3.5 logs |
|  |  |  |  | VRE | 4.2 logs |
| Medium Fan = #2 | 80 ppm | 1.0% | 30 mins. | MRSA | No kill |
|  |  |  |  | VRE | 2.3 logs |
| High Fan = #3 | 80 ppm | 1.0% | 30 mins. | MRSA | No kill |
|  |  |  |  | VRE | No kill |

Each of the foregoing data points are average values derived from 6 independent runs using two different bacteria at a concentration in excess of 6 logs. For the "No Current" control runs, there was 100% kill in all cases. The air current was created using a common commercial fan with four speed settings (0, #1, #2, #3). The fan was placed at an oblique angle to the specimen discs (45 degrees) at a distance of 90 cms. These data clearly indicate that in a contaminated space, the ability the kill bacteria, using the ozone-peroxide protocol of the invention, is inversely proportional to the air current strength directed over a contaminated surface.

CONCLUSION

The data provided in the above Tables clearly demonstrate that the process according to the invention is capable of completely eliminating bacteria contained within biofilm preparations on a non-porous hardened surface such as stainless steel. Although small adjustments in the time of exposure are necessary for the common pathogens found in hospital settings (25-45 minutes), *Bacillus subtilis* and therefore its cousin anthrax require almost twice the exposure time, but these pathogens are of little concern to hospitals.

Thus one aspect of the invention is a process for disinfecting a room, which comprises introducing into the room an oxygen/ozone/hydrogen peroxide gas mixture, optionally raising the pressure within the room above atmospheric pressure, physically agitating fibrous and porous surfaces within the room while the surfaces are exposed to the ozone and hydrogen peroxide containing atmosphere of relative humidity at least 65%, returning the room to atmospheric pressure, and removing the residual ozone and hydrogen peroxide from the room's atmosphere, respectively down to a maximum level of 0.04 ppm and below the level of 1.00 ppm.

Another aspect of the invention is a portable system for disinfecting rooms and surfaces therein with ozone and hydrogen peroxide, comprising an oxygen container, a hydrogen peroxide generator, an ozone generator fed with medical grade oxygen from the oxygen container and discharging a mixture of oxygen and ozone, an ozone controller adapted to control the proportion of ozone in the mixture of oxygen and ozone, a hydrogen peroxide controller adapted to control the amount of hydrogen peroxide generated, a discharge tube to receive the mixture of oxygen and ozone from the ozone generator and hydrogen peroxide from the hydrogen peroxide generator, the discharge tube having an outlet end, optionally a physical agitation system at the outlet end of the discharge tube, for physical agitation of surfaces with oxygen/ozone/hydrogen peroxide mixture issuing therefrom, pressure adjusting means connected to the ozone generator arranged to adjust the pressure of the oxygen/hydrogen peroxide/ozone mixture discharged by the physical agitation system and the oxygen/hydrogen peroxide/ozone gas pressure in the room under treatment, temperature adjusting means connected to the ozone generator arranged to adjust the temperature of the oxygen/hydrogen peroxide/ozone mixture discharged by the physical agitation system, humidity adjusting means adapted to humidify the treatment location to a relative humidity not less than 65%, and an ozone remover and hydrogen peroxide remover adapted to receive oxygen/hydrogen peroxide/ozone mixture from the environment of use of the discharge tube and to remove ozone and hydrogen peroxide from the mixture.

The invention claimed is:

1. A process of combating bacteria in an enclosed space within a room and contained in biofilm on surfaces within the room, the process conducted in the room at atmospheric pressure and consisting of:

creating in the room at atmospheric pressure, a disinfecting atmosphere which includes ozone at a concentration of 2-350 ppm by weight and hydrogen peroxide at an amount of 0.2-10 wt. %, at a relative humidity of at least 60%, wherein said amount of hydrogen peroxide is derived from a supply solution of 0.2-10% hydrogen peroxide, wherein the disinfecting atmosphere is moved about the room;

subjecting the biofilm, including at least biofilm carrying surfaces having live bacteria therein, to said disinfecting atmosphere at atmospheric pressure for a period of time effective to cause substantial kill, by at least a 6 log reduction, of the bacteria in the biofilm, the period of time being at least 30 minutes, wherein the step of moving the disinfecting atmosphere about the room is suspended for up to about 60% of said period of time; and subsequently removing ozone from the disinfecting atmosphere, down to 0.04 ppm or less and removing hydrogen peroxide from the disinfecting atmosphere down to less than 1.00 ppm or less.

2. The process of claim 1 wherein the period of time during which the biofilm is subjected to the disinfecting atmosphere is from about 30 minutes to about 120 minutes.

3. The process of claim 1 wherein the ozone concentration in the disinfecting atmosphere is from 20 to 350 ppm by weight.

4. The process of claim 1 wherein the ozone concentration in the disinfecting atmosphere is from 20 to 200 ppm by weight.

5. The process of claim 1 wherein the ozone concentration in the disinfecting atmosphere is from 10-100 ppm by weight.

6. The process of claim 1 wherein the ozone concentration in the disinfecting atmosphere is from 35-100 ppm by weight.

7. The process of claim 1 wherein the ozone concentration in the disinfecting atmosphere is from 20-90 ppm by weight.

8. The process of claim 1 wherein the ozone concentration in the disinfecting atmosphere is from 35-80 ppm by weight.

9. The process of claim 1 wherein the hydrogen peroxide amount in the disinfecting atmosphere is from 1.0-5 wt. %.

10. The process of claim 1 wherein the period of time during which the biofilm is subjected to the disinfecting atmosphere is from 60 to 105 minutes.

11. The process of claim 1 wherein the bacteria subjected to the disinfecting atmosphere and substantially killed includes *Clostridium difficile* (*C. difficile*), *E. coli; Pseudomonas aeruginosa*, methicillin-resistant *Staphylococcus aureus* (MRSA), vancomycin-resistant *Enterococcus* (VRE), *Bacillus subtilis, Bacillus anthracis* or combinations of two or more of said bacteria.

12. The process of claim 1 wherein the step of moving the disinfecting atmosphere about the room is suspended for up to about 50% of said period of time.

13. The process of claim 1 wherein the step of moving the disinfecting atmosphere about the room is suspended for up to about 40% of said period of time.

14. The process of claim 1 wherein the step of moving the disinfecting atmosphere about the room is suspended for about from 20% to 40% of said period of time.

15. The process of claim 1 wherein the step of moving the disinfecting atmosphere about the room is suspended for a plurality of time intervals during said period of time.

16. The process of claim 1 wherein the room is sealed against movement of fluid into or out from the room.

* * * * *